US012403213B2

(12) United States Patent
Locke et al.

(10) Patent No.: US 12,403,213 B2
(45) Date of Patent: Sep. 2, 2025

(54) WOUND DRESSING WITH SELECTIVE AND DYNAMIC TRANSPARENCY (71) Applicant: Solventum Intellectual Properties Company, Maplewood, MN (US)

(72) Inventors: Christopher B. Locke, Bournemouth (GB); Timothy M. Robinson, Wimbourne (GB)

(73) Assignee: Solventum Intellectual Properties Company, Maplewood, MN (US)

(*) Notice: Subject to any disclaimer, the term of this patent is extended or adjusted under 35 U.S.C. 154(b) by 914 days.

(21) Appl. No.: 17/421,293

(22) PCT Filed: Jan. 9, 2020

(86) PCT No.: PCT/US2020/012901
§ 371 (c)(1),
(2) Date: Jul. 7, 2021

(87) PCT Pub. No.: WO2020/154107
PCT Pub. Date: Jul. 30, 2020

(65) Prior Publication Data
US 2022/0072193 A1 Mar. 10, 2022

Related U.S. Application Data (60) Provisional application No. 62/795,714, filed on Jan. 23, 2019.

(51) Int. Cl.
A61F 13/02 (2024.01)
A61F 13/00 (2024.01)
(Continued)

(52) U.S. Cl.
CPC ........ *A61L 15/425* (2013.01); *A61F 13/0243* (2013.01); *A61F 13/05* (2024.01); *A61L 15/24* (2013.01); *A61F 2013/00182* (2013.01)

(58) Field of Classification Search
CPC .... A61L 15/425; A61L 15/24; A61F 13/0243; A61F 13/05; A61F 2013/00182;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 650575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

Primary Examiner — Rebecca E Eisenberg
Assistant Examiner — Ted Yang (57) ABSTRACT A selectively transparent wound therapy dressing, system, and method of use are provided. The dressing may include conformable foam and drape layers, wherein the drape layer has a refractive index substantially within a range of a disclosing liquid. When the disclosing liquid is applied to the drape layer, the drape layer may switch from opaque to transparent. Subsequent evaporation of the disclosing liquid may return the drape layer to an opaque state. Some embodiments provide for paired use with a negative pressure source input device. The method of use provides selective visibility of a treatment site, and reduces the amount of time in which a patient views an acute or traumatic wound or injury.

17 Claims, 9 Drawing Sheets (51) Int. Cl.
  *A61F 13/05* (2024.01)
  *A61L 15/24* (2006.01)
  *A61L 15/42* (2006.01)

(58) Field of Classification Search
  CPC ............... A61F 13/0233; A61F 13/023; A61F 2013/00089; A61F 13/00055; A61F 13/00059; A61F 13/02; A61F 2013/15073
  See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,480,377 A * | 1/1996 | Cartmell ................. A61L 15/60 602/42 |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,637,080 A * | 6/1997 | Geng .................... A61F 13/023 602/42 |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Teaton et al. |
| RE47,452 E * | 6/2019 | Bui .......................... A61L 31/10 |
| 2002/0019602 A1 * | 2/2002 | Geng ................ A61F 13/0226 602/41 |
| 2002/0077661 A1 | 6/2002 | Saadat |
| 2002/0091347 A1 * | 7/2002 | Eakin ................ A61F 13/00055 602/41 |
| 2002/0115951 A1 | 8/2002 | Norstrem et al. |
| 2002/0120185 A1 | 8/2002 | Johnson |
| 2002/0143286 A1 | 10/2002 | Tumey |
| 2008/0021381 A1 * | 1/2008 | Lurvey ................. A61M 39/16 604/87 |
| 2009/0216170 A1 * | 8/2009 | Robinson ............ A61F 13/0246 602/60 |
| 2010/0291058 A1 * | 11/2010 | Bowlin .................... A61P 17/02 428/401 |
| 2011/0189463 A1 * | 8/2011 | Moore ................... A61B 46/40 442/400 |
| 2011/0257612 A1 * | 10/2011 | Locke ...................... A61F 13/05 604/319 |
| 2012/0143155 A1 * | 6/2012 | Edvardsen ............. A61F 5/443 604/318 |
| 2012/0330252 A1 * | 12/2012 | Stokes ...................... G01L 1/24 604/318 |
| 2014/0094730 A1 * | 4/2014 | Greener ............ A61F 13/01038 602/44 |
| 2014/0336557 A1 * | 11/2014 | Durdag ................. A61L 15/26 604/319 |
| 2015/0351970 A1 * | 12/2015 | Dagger ............ A61F 13/00059 604/361 |
| 2015/0351971 A1 * | 12/2015 | Simmons ................ A61L 15/56 602/54 |
| 2016/0262672 A1 * | 9/2016 | Hammond ......... A61B 5/14539 |
| 2017/0143553 A1 * | 5/2017 | Bogue ............ A61F 13/00059 |
| 2017/0189237 A1 * | 7/2017 | Locke .................... A61F 13/05 |
| 2018/0235816 A1 | 8/2018 | Hartwell |
| 2019/0083322 A1 * | 3/2019 | Huang ................... A61F 13/05 |
| 2019/0212311 A1 * | 7/2019 | Hammond ......... A61B 5/14539 |
| 2019/0336343 A1 * | 11/2019 | Etchells ............ A61F 13/00055 |
| 2020/0008981 A1 * | 1/2020 | Wheldrake ......... A61F 13/0209 |
| 2020/0164616 A1 * | 5/2020 | Carlyle ..................... B32B 7/02 |

(56) References Cited

U.S. PATENT DOCUMENTS

| | | | |
|---|---|---|---|
| 2020/0172433 A1* | 6/2020 | Haghanifar | C03C 17/30 |
| 2020/0400581 A1* | 12/2020 | Jiang | C08J 9/26 |
| 2021/0052432 A1* | 2/2021 | Buan | A61F 13/022 |
| 2022/0023103 A1* | 1/2022 | Locke | A61F 13/05 |
| 2022/0117790 A1* | 4/2022 | Locke | A61F 13/01008 |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| DE | 20 2017 005 574 U1 | 1/2018 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 0 528 091 B1 | 2/1993 | |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2011/003421 A1 | 1/2011 | |
| WO | WO-2017151226 A1 * | 9/2017 | A61F 13/00068 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion for International Application No. PCT/US2020/012889 dated Mar. 20, 2020 (13 pages).

International Search Report and Written Opinion on International Patent Application No. PCT/US2020/012901 dated Apr. 17, 2020 (16 pages).

\* cited by examiner

WOUND DRESSING WITH SELECTIVE AND DYNAMIC TRANSPARENCY

CROSS-REFERENCE TO RELATED APPLICATIONS

This application is a US national phase application under 35 USC § 371 of International Application No. PCT/US2020/012901 filed on Jan. 9, 2020, which claims the benefit of priority to U.S. Provisional Application No. 62/795,714, entitled "WOUND DRESSING WITH SELECTIVE AND DYNAMIC TRANSPARENCY" filed on Jan. 23, 2019, which are both incorporated herein by reference in their entireties.

TECHNICAL FIELD

The invention set forth in the claims relates generally to tissue treatment and more particularly, but without limitation, to dressings for tissue treatment and methods for using the dressings for tissue treatment both with and without negative pressure.

BACKGROUND

The present disclosure relates generally to tissue treatment systems and, more particularly, to a wound dressing with selective and dynamic transparency.

Clinicians and patients often have different desires for visualization of wounds and treatment sites. Patients often do not wish to see a wound or the peri-wound, as it can be upsetting or cause anxiety. Clinicians and medical practitioners, on the other hand, often need to view a wound or treatment site to check the wound condition and look for signs of treatment progression and healing indicators (e.g., redness, inflammation, maceration, etc.).

Most wound dressings are either partially or fully occlusive. This makes it difficult for clinicians to view the progress of treatment. However, with selectively or dynamically transparent dressings clinicians can more accurately manage wound care. For example, dynamic transparency allows a clinician to gauge the amount of fluids or exudate in a region of the wound. Visualization of the periwound is also crucial in judging healing progression and possible infection. Moreover, a wound dressing and system with selective transparency—i.e., one that can be switched "on" and "off"—may also allow clinicians and medical practitioners to place, and later locate, bio-sensors and indicators under a drape.

Thus, an improved dressing, system, and method that allows a medical practitioner or physician to view a wound or treatment site when desired and occlude the wound or treatment site at all other times is needed.

SUMMARY

The present disclosure overcomes the drawbacks of previously-known systems by providing an improved dressing, system, and method for selective visualization of a wound or periwound. The wound therapy dressing may include a foam layer, and a drape layer having a material with a refractive index substantially within a range of 1.3 to 1.55. The wound therapy dressing may also have a foam layer that is substantially transparent. In one embodiment of the wound therapy dressing, the foam layer may be white. The wound therapy dressing may also include a drape layer having a fabric comprising fine fibered polymers. In some embodiments, the fine fibered polymers may be elastic materials, including polyvinylidene fluoride (PVF), polyvinylidene difluoride (PVDF), ethylene-vinyl acetate, thermoplastic polyurethane, thermoplastic elastomer, thermoplastic vulcanizate, polyether block amide, polyamides, polyethyleneimines, or polyester. In other embodiments, the drape layer may be made of porous or microporous particles, including minerals or polymers. In some embodiments, the minerals may be silica, silicates, fluorites, or fluorides. In other embodiments, the polymers of the microporous drape layer may be fluoropolymers, silicones, or acrylics.

In accordance with yet another aspect of the present disclosure, a wound therapy system is provided. The system may include a conformable, transparent foam dressing layer, and a conformable drape layer configured to extend over and adhere the transparent foam dressing layer to a treatment site. In a first state the drape layer may be opaque, in a second state, the drape layer may become transparent when a disclosing liquid with a refractive index within a range of the refractive index of the drape layer is applied to the drape layer, the second state occurring at a point in time subsequent to the first state, and in a third state, the drape layer may become opaque again as the disclosing liquid evaporates, the third state occurring at a point in time subsequent to the second state.

The wound therapy system further may include a negative pressure wound input device. In one embodiment, the wound therapy system may couple to a hole in the drape layer through which air may be withdrawn from the treatment site. The drape layer of the wound therapy system further may be a fabric comprising fine fibered polymers. The fine fibered polymers may be elastic materials, such as polyvinylidene fluoride (PVF), polyvinylidene difluoride (PVDF), ethylene-vinyl acetate, thermoplastic polyurethane, thermoplastic elastomer, thermoplastic vulcanizate, polyether block amide, polyamides, polyethyleneimines, or polyester. In some embodiments, the fine fibered polymers may be plasma or corona surface treated. Further, the fine fibered polymers may have diameters from about less than 1 micrometer to about 30 micrometers. The fine fibered polymers may be manufactured from dry laid, airlaid, or woven manufacturing methods.

In certain embodiments, a patient facing side of the drape layer further may have an about 5 micrometer to about 20 micrometer breathable polyurethane coating to enhance water proofing. The drape layer may also have an adhesive coat that can bond to either the transparent foam dressing layer, or, alternatively, directly to periwound or wound treatment sites. In some embodiments, the adhesive is one of an acrylic, polyurethane, or a silicone gel. The drape layer may also be made of microporous or porous particles. In some embodiments, the porous particles may be minerals or polymers. Some exemplary minerals include, but are not limited to, silica, silicates, fluorites, or fluorides. Some exemplary polymers include, but are not limited to, fluoropolymers, silicones or acrylics.

In some embodiments, the disclosing liquid used to saturate the drape layer may have a refractive index between about 1.0 to about 2.0. In some embodiments, the disclosing liquid used to saturate the drape layer may have a refractive index between about 1.2 to about 1.75. In some embodiments, the disclosing liquid used to saturate the drape layer may have a refractive index between about 1.33 to about 1.55. Further, the disclosing liquid may be fluorinated ethylene propylene polymer (FEP). In other embodiments, the disclosing liquid may be water or ethanol or any combination of water and ethanol. The disclosing liquid further may be ethanol and benzyl alcohol.

The drape layer may be polyvinylidene difluoride (PVDF) bonded to a drape cover with the PVDF fused to the drape through heat lamination.

In certain embodiments, an island dressing may be used in lieu of a foam dressing. The drape layer may also be interposed between multiple wound dressing layers. In the first state, the drape layer also may appear frosted. In certain embodiments, the foam pore sizes are less than or equal to one hundred (100) micrometers. Moreover, the drape layer also may be a foam with pore sizes less than or equal to 100 micrometers. In other embodiments, the drape layer may include two layers of polymeric polarizing filter. The drape layer further may include a pH indicator. The pH indicator may be phenolphthalein. In certain of these embodiments, an acid disclosing agent may be wiped over the drape layer. The acid disclosing agent also may be carbonated water or ethanol in concentration with carbonated water.

In accordance with yet another aspect of the present disclosure, a method for providing wound therapy is provided. The method may include: (i) applying to a treatment site a wound therapy system that includes a conformable, transparent foam dressing layer, and a conformable, selectively-transparent drape layer configured to extend over and adhere the transparent foam dressing layer to a treatment site; (ii) applying a disclosing liquid with a refractive index within a range of the refractive index of the drape layer to the drape layer, allowing the selectively-transparent drape layer to change from an opaque state to a transparent state; (iii) observing the treatment site while the drape layer remains in the transparent state; and (iv) allowing the disclosing liquid to evaporate, which allows the drape layer to return to an opaque state.

Using the treatment method, a patient may only see the treatment site while being examined by a medical practitioner or physician. A medical practitioner also may monitor healing at the periwound of a treatment site using this method. In some embodiments, the system further may include a negative pressure wound input device. In certain of these embodiments, the negative pressure wound input device may couple to a hole in the drape layer through which air is withdrawn from the treatment site.

DETAILED DESCRIPTION

Wound Therapy Dressing:

A wound therapy dressing is provided herein. In certain embodiments, the wound therapy dressing illustratively may include a foam layer, and a drape layer wherein the drape layer is made of a material having a refractive index substantially within a range of 1.3 to 1.55. As used herein, the terms "substantially," "substantial," and "about" are used to describe and account for small variations. When used in conjunction with a material or a standard, the terms can refer to instances in which the standard or material occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Figure 1:
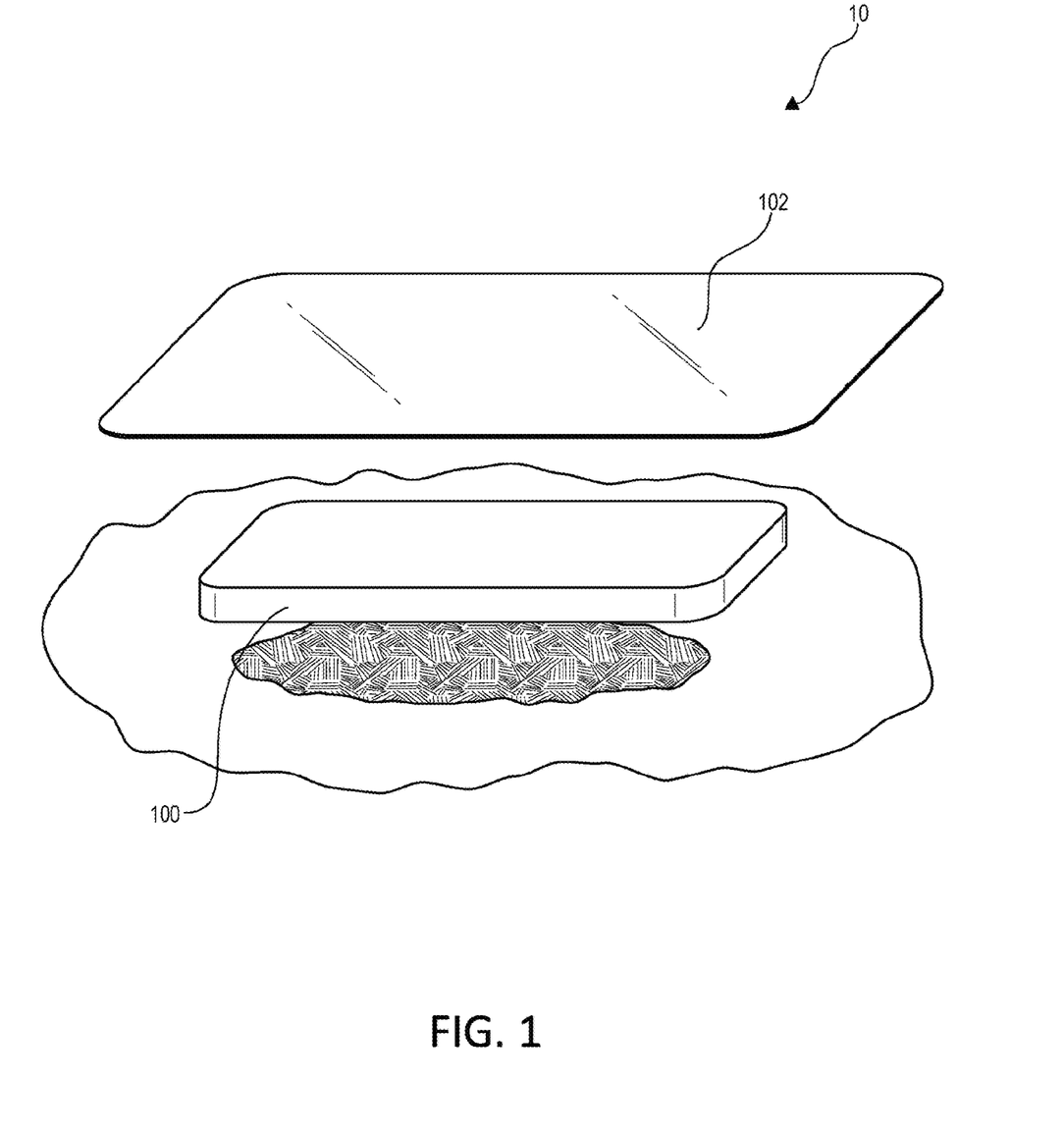
FIG. 1 illustrates an exploded view from a roughly forty-five degree angle of an embodiment of the wound therapy dressing.

Referring to FIG. 1, an exemplary wound therapy dressing 10 in accordance with the principles of the present disclosure is described. Wound therapy dressing 10 may include foam layer 100 and drape layer 102, wherein drape layer 102 has a refractive index substantially within a range of 1.3 to 1.55. Foam layer 100 may be substantially transparent, or non-transparent. Foam layer 100 further may be white.

Figure 2:
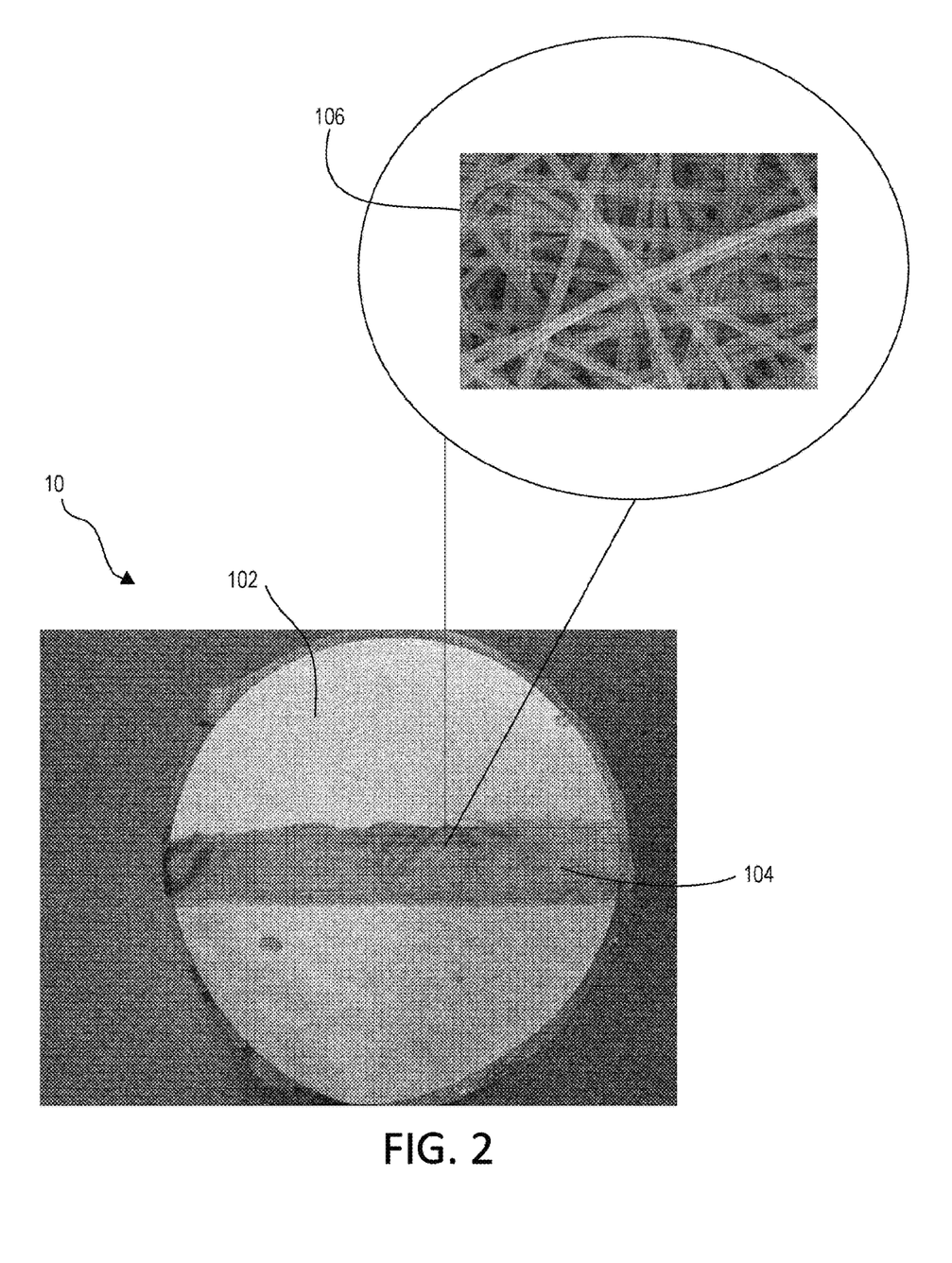
FIG. 2 depicts the wound therapy dressing wherein the foam layer comprises fine fibered polymers.

As shown in FIG. 2, drape layer 102 may be made of fabric 104 comprising fine fibered polymers 106. Fine fibered polymers 106 also may be elastic or any suitable Modulus to fit securely overly a wound bed. In certain embodiments, the elastic materials may include, but are not limited to: polyvinylidene fluoride (PVF), polyvinylidene difluoride (PVDF), ethylene-vinyl acetate, thermoplastic polyurethane, thermoplastic elastomer, thermoplastic vulcanizate, polyether block amide, polyamides, polyethyleneimines, or polyester.

Figure 3A:
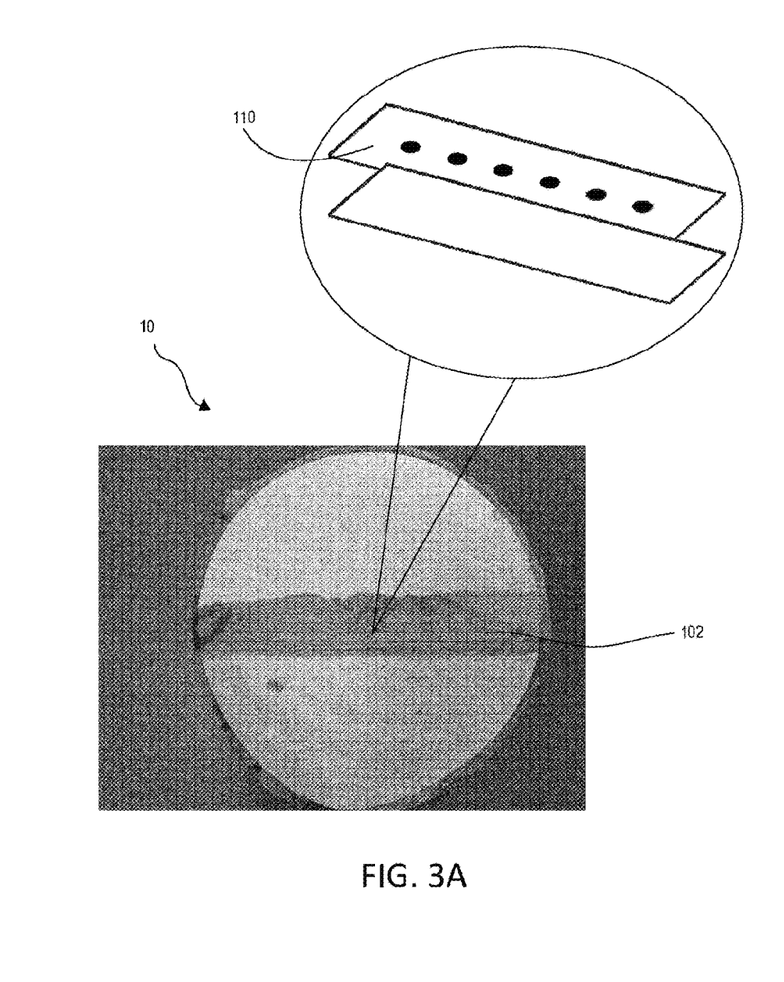
FIGS. 3A and 3B depict two possible embodiments where the drape layer is made up of porous particles.
Figure 3B:
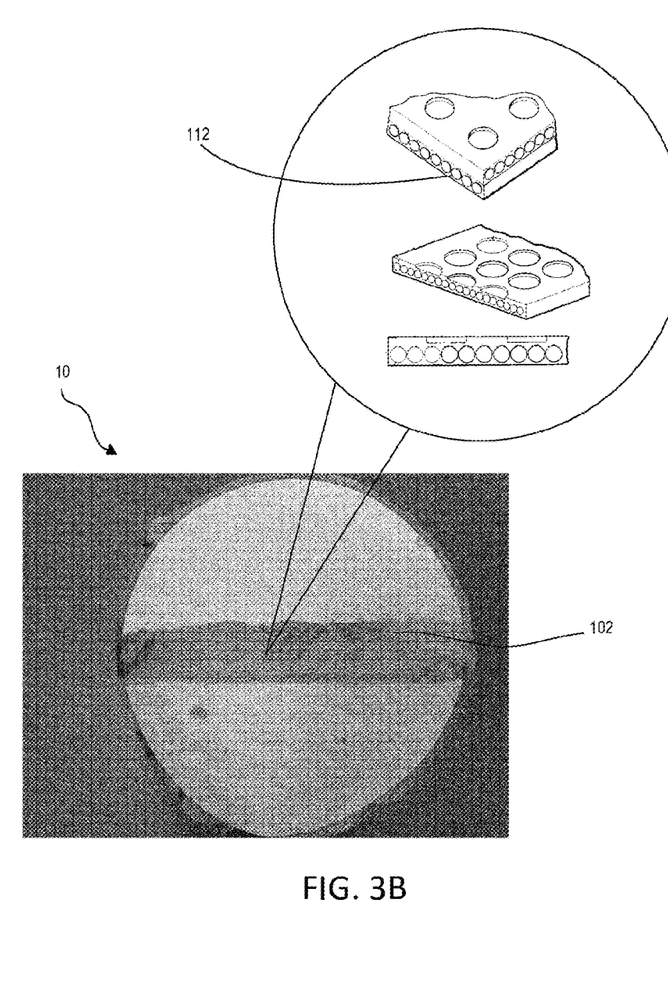

Referring to FIG. 3A and FIG. 3B, wound therapy dressing 10 also may have drape layer 102 made of porous particles 110 or microporous particles 112. In some embodiments, porous particles 110 or microporous particles 112 further may be minerals or polymers. Exemplary minerals include, but are not limited to, silica, silicates, fluorites, or fluorides. Exemplary polymers include, but are not limited to, fluoropolymers, silicones, or acrylics.

Figure 4A:
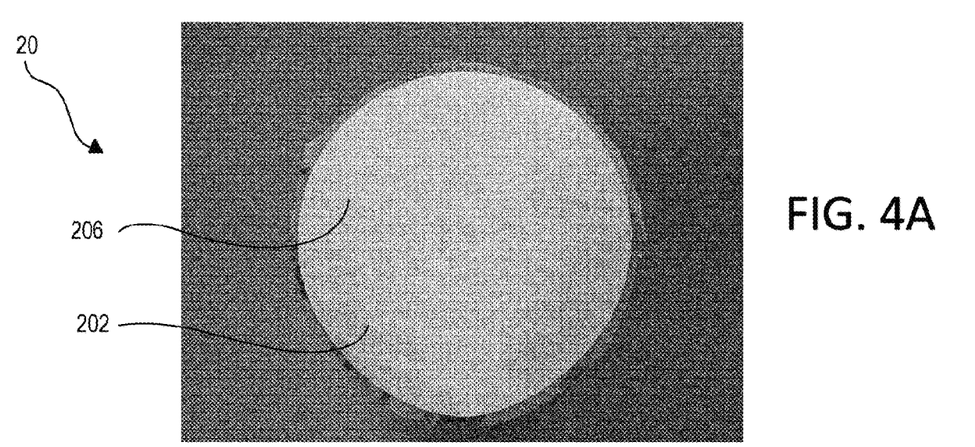
FIGS. 4A through FIG. 4C demonstrate the transition from a first state where the drape layer is opaque to a second state, where the drape layer becomes transparent when a disclosing liquid is applied, to a third state, where the drape layer returns to opaque as the disclosing liquid evaporates.
Figure 4B:
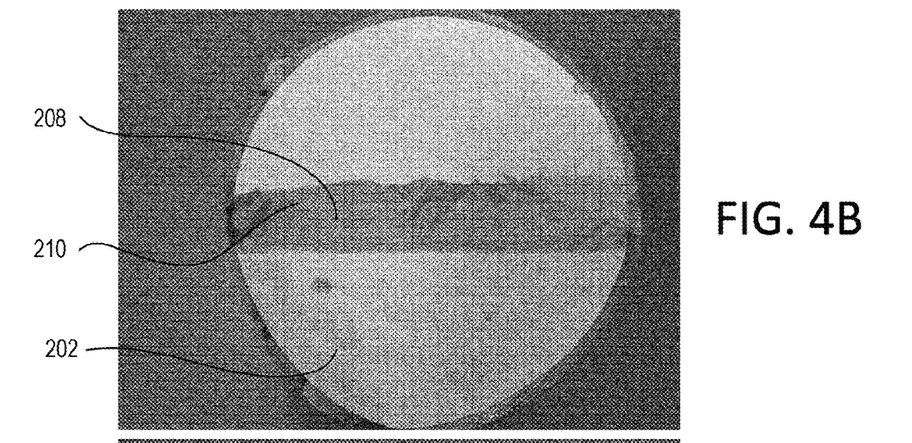

Wound Therapy System:

A wound therapy system is also provided herein. Referring to FIGS. 4A-4C and FIGS. 5A-5B, in one embodiment, wound therapy system 20 may include conformable foam dressing layer 200 and conformable drape layer 202. Conformable drape layer 202 may be configured to extend over and adhere foam dressing layer 200 to treatment site 204 or wound bed, which further may include periwound 205. The treatment site may be a wound bed. Referring to FIG. 4A, in first state 206 drape layer 202 is opaque. Referring to FIG.

Figure 4C:
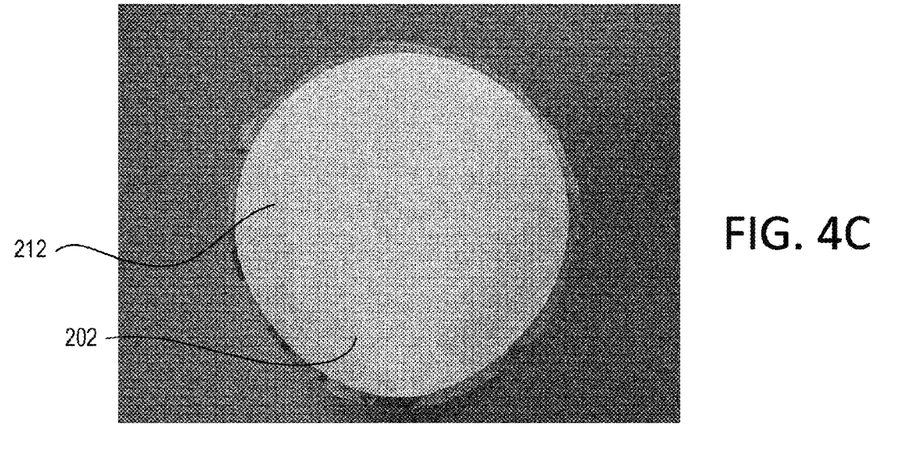
Figure 5A:
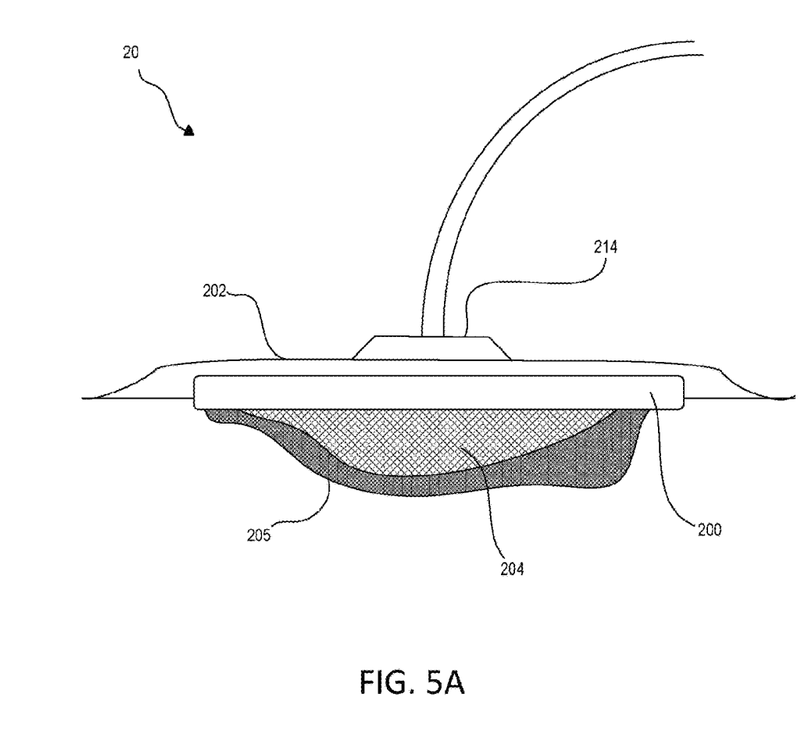
FIG. 5A shows a side view of the wound therapy system, including a negative pressure input device, applied on a treatment site.
Figure 5B:
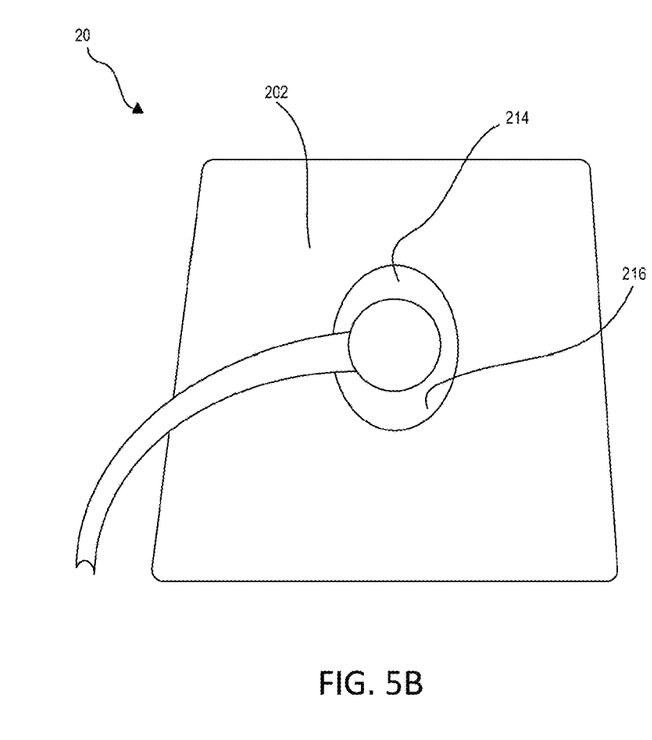
FIG. 5B illustrates a top view of an embodiment of the wound therapy system that includes the negative pressure input device.

4B, in second state 210, drape layer 202 becomes transparent when disclosing liquid 210 with a refractive index within a range of the refractive index of drape layer 202 is applied to drape layer 202. Second state 206 occurs at a point in time subsequent to first state 206. Referring to FIG. 4C, in third state 212, drape layer 202 becomes opaque again as disclosing liquid 210 evaporates. Third state 212 occurs at a point in time subsequent to second state 210. Wound therapy system 20 further may have negative pressure wound input device 214, as shown from a side view in FIG. 5A. As further shown in FIG. 5B, negative pressure wound input device 214 may couple to hole 216 in drape layer 202 through which air may be withdrawn from treatment site 204. Either or both conformable foam dressing layer 200 and conformable drape layer 202 may be transparent or selectively-transparent.

Drape layer 202 may be made of fabric 104, which further may comprise fine-fibered polymers. The fine-fibered polymers 106 of wound therapy system 20 may be elastic materials. In certain embodiments, exemplary elastic materials may include, but are not limited to: polyvinylidene fluoride (PVF), polyvinylidene difluoride (PVDF), ethylene-vinyl acetate, thermoplastic polyurethane, thermoplastic elastomer, thermoplastic vulcanizate, polyether block amide, polyamides, polyethyleneimines, or polyester. Fine-fibered polymers of wound therapy system 20 also may be plasma or corona surface treated. In some embodiments, fine-fibered polymers of wound therapy system 20 may have diameters from about less than 1 micrometer to about 30 micrometers. In some embodiments, the polymers may be manufactured from dry laid, airlaid, or woven manufacturing methods. In certain embodiments, a patient facing side of drape layer 202 further has an about 5 micrometer to an about 20 micrometer breathable polyurethane coating to enhance water proofing. Drape layer 202 also may include an adhesive coating that can bond to either foam dressing layer 200 or directly to periwound 205. In some embodiments, the adhesive may be an acrylic, polyurethane, or a silicone gel. Drape layer 202 may also be made of porous or microporous particles. In certain embodiments, the porous particles may be minerals or polymers. Exemplary minerals may include, but are not limited to: silica, silicates, fluorites, or fluorides. Exemplary polymers may include, but are not limited to: fluoropolymers, silicones, or acrylics.

Disclosing liquid 210 may have a range of refractive indexes, including, but not limited to, a range between about 1.0 and about 2.0, between about 1.2 and about 1.75, or between about 1.33 and 1.35. If the refractive index of disclosing liquid 210 and drape 202 are close, as air is displaced more transparency may be achieved in drape 202. Disclosing liquid 210 further may be fluorinated ethylene propylene polymer (FEP). In some embodiments, disclosing liquid 210 is water or any combination of water and ethanol. Disclosing liquid 210 also may be ethanol or benzyl alcohol. In one particular embodiment, drape layer 202 is polyvinylidene difluoride (PVDF) bonded to a drape cover and the PVDF is fused to the drape cover through heat lamination. An island dressing also may be used in lieu of or in combination with a foam dressing.

Figure 6:
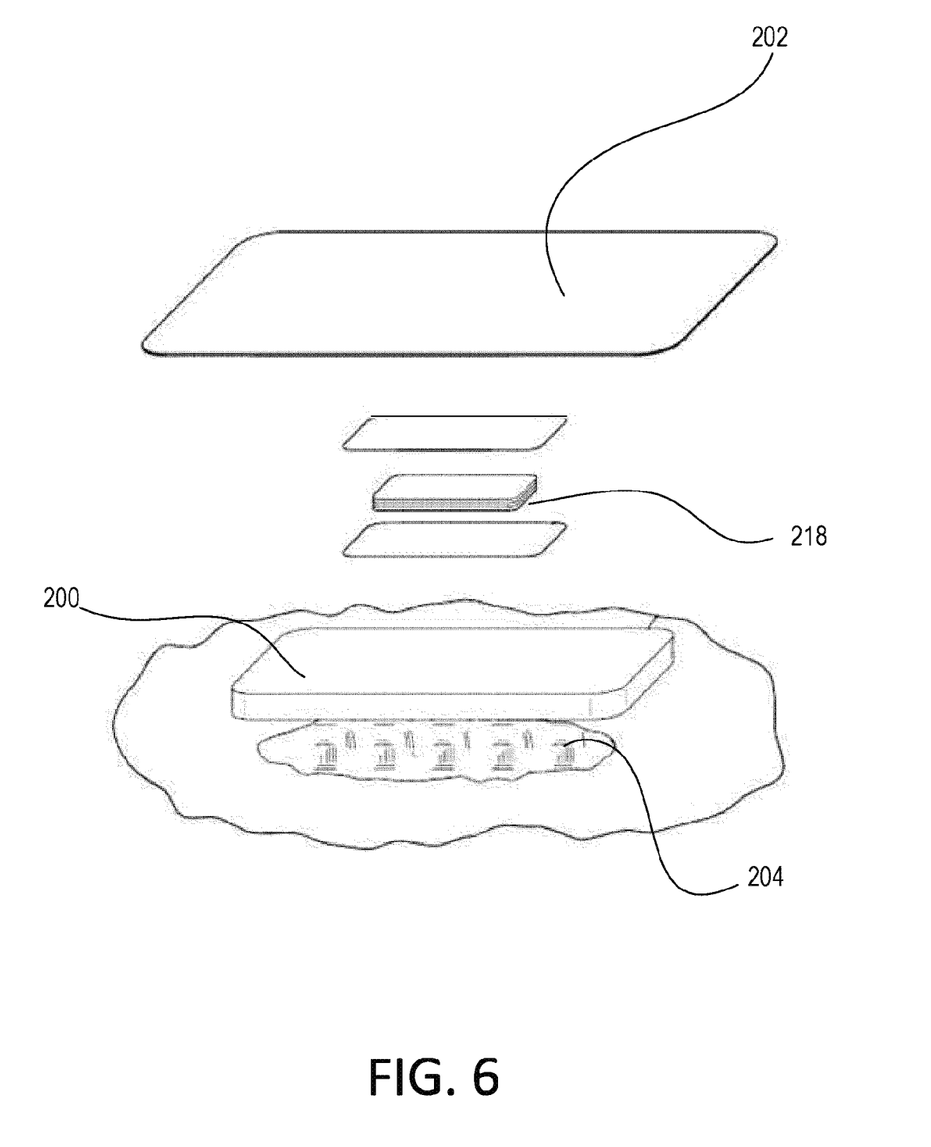
FIG. 6 shows an embodiment of the wound therapy system where the selectively transparent drape layer is interposed within, around, on top of, or between multiple wound dressing layers.

Referring now to FIG. 6, drape layer 202 is shown disposed above or on top of a plurality of wound dressing layers 218. In other embodiments, drape layer 202 may be interposed within, around, or between more than one other wound dressing layer. In some embodiments, drape layer 202 may appear frosted or partially frosted in first state 206. The pore sizes of foam dressing layer 200 may be less than or equal to 100 micrometers. Additionally, draper layer 202 also may be a foam composite and can also have pore sizes less than or equal to 100 micrometers.

Figure 7:
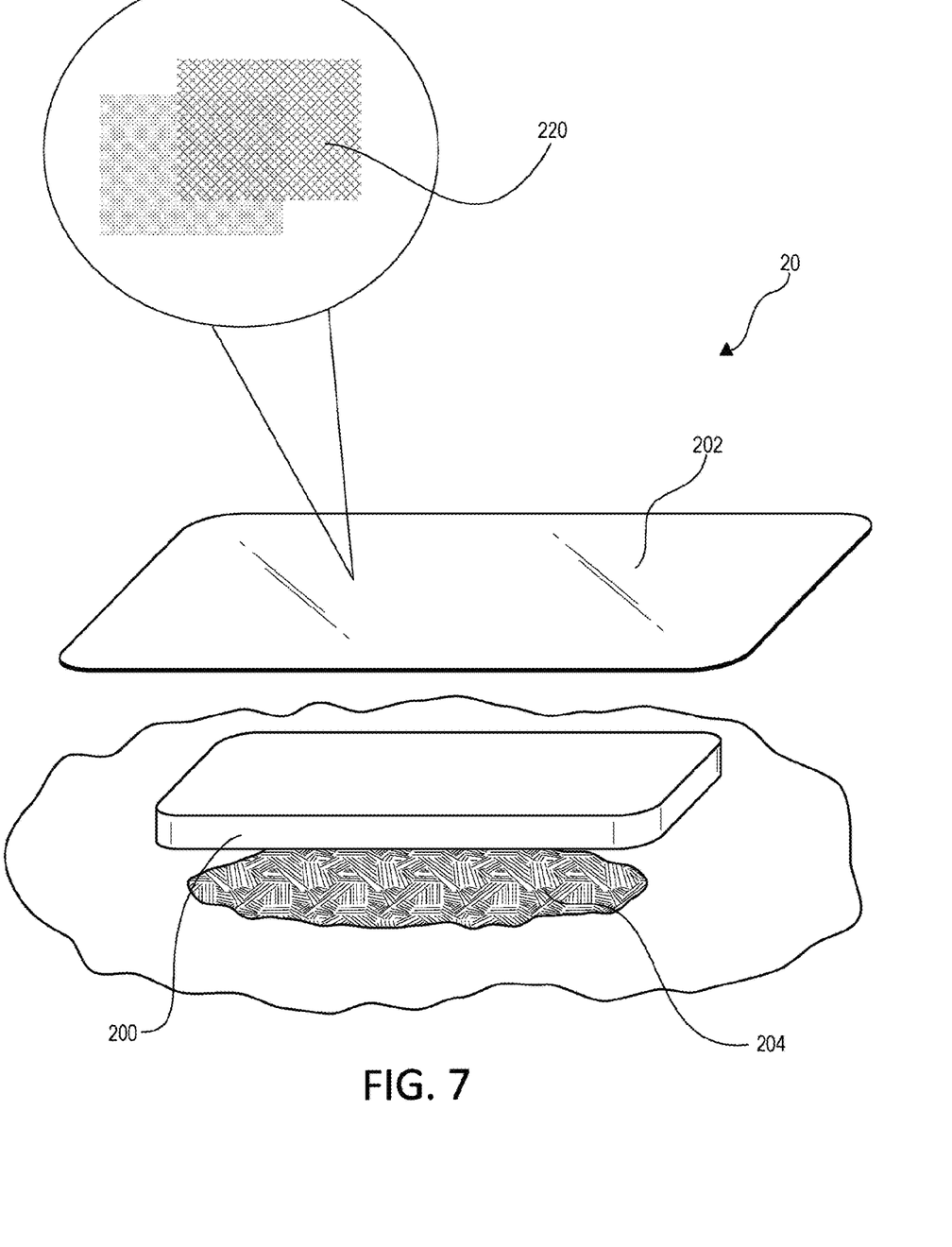
FIG. 7 illustrates an embodiment of the wound therapy system where the drape layer is made of at least two layers of polymeric polarizing filter.
Figure 8:
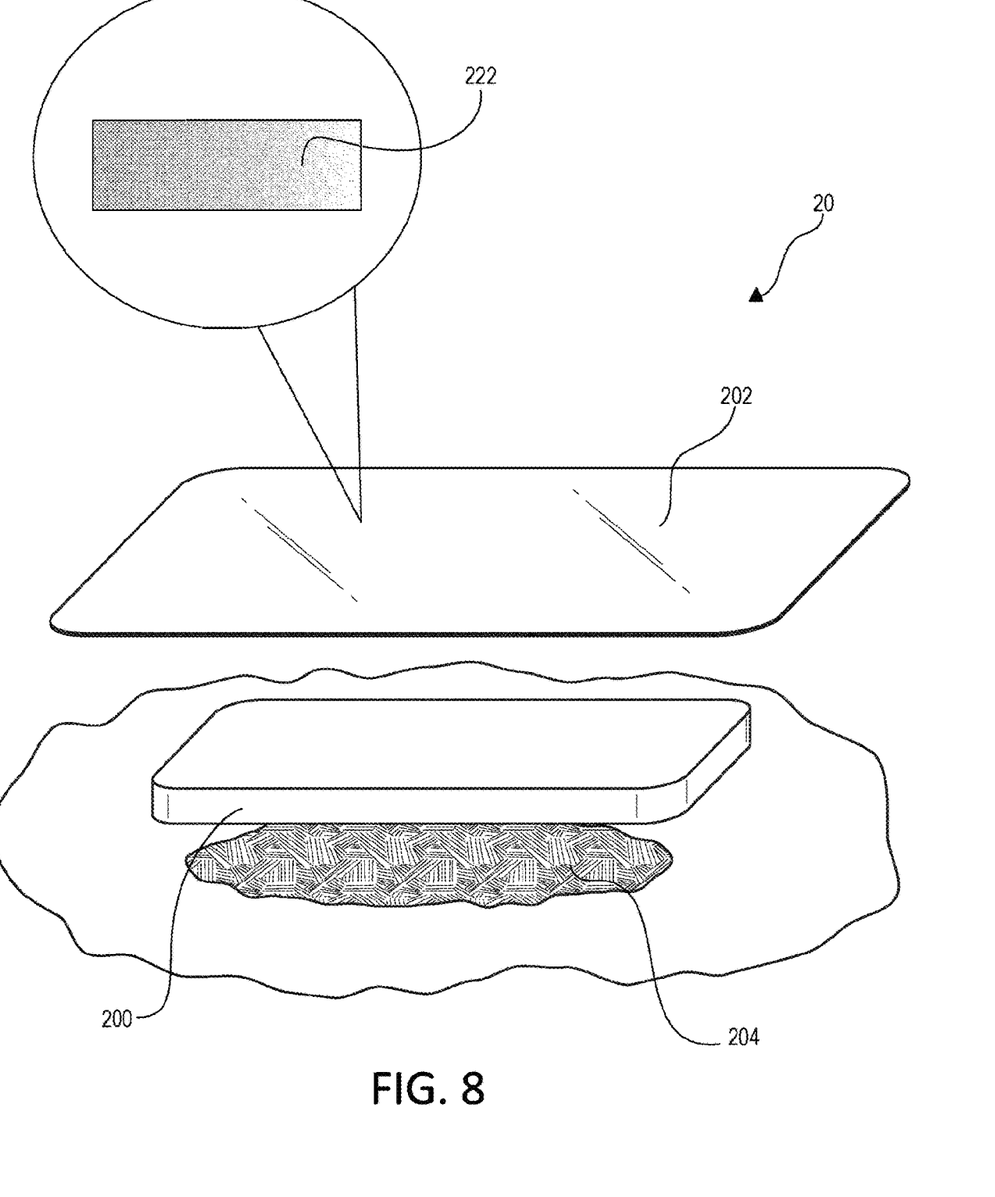
FIG. 8 depicts an embodiment of the wound therapy system where the drape layer further includes a pH indicator.

Referring now to FIG. 7, drape layer 202 also may include two or more layers of polymeric polarizing filter 220. As further shown in FIG. 8, drape layer 202 also may include pH indicator 222. A cationic polymer, such as polyethyleneimine may be mixed with a cover film, or coated on with a pH indicator, such as phenolphthalein which can provide a deep pink hiding color to block visibility of wound treatment site 204 or periwound 205. If an acid is used as disclosing liquid 210 and wiped over drape 202, pH indicator 222 may become clear. One suitable volatile acid may be carbonated water. Ethanol may be added to the carbonated water to increase its volatility.

Figure 9A:
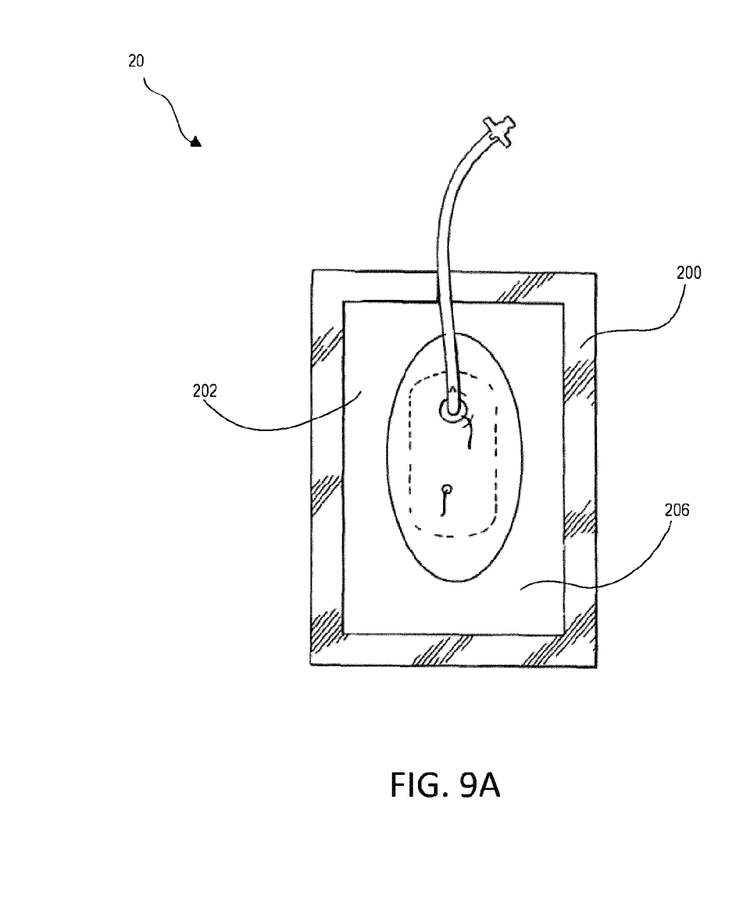
FIG. 9A and FIG. 9B illustrate a method for wound therapy wherein the wound therapy system is applied to a treatment site and a disclosing liquid with a refractive index within a range of the refractive index of the drape layer is applied to change the drape from an opaque state to a transparent state.
Figure 9B:
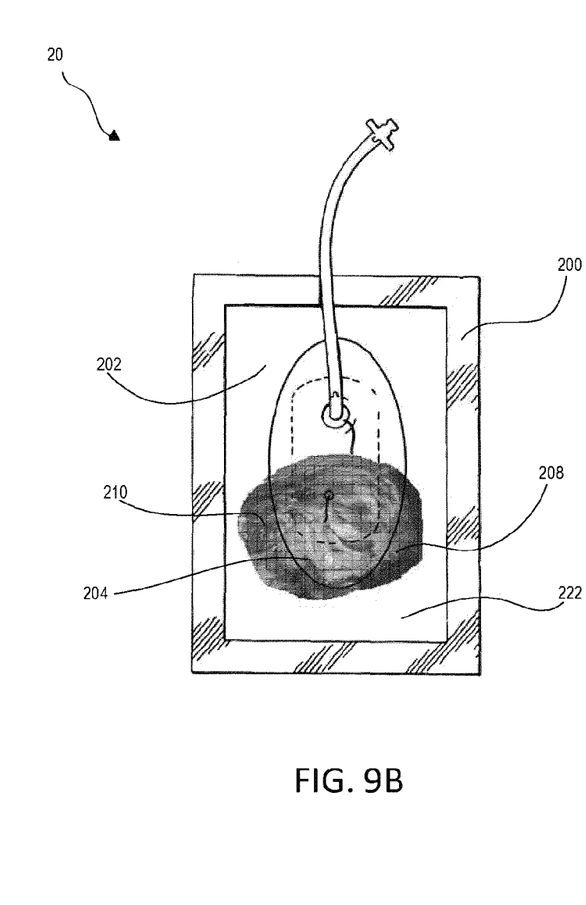

Method of Use:

A method for wound therapy is also provided herein. Referring to FIG. 9A and FIG. 9B, the method may include: i) applying to treatment site 204 conformable foam dressing 200 and conformable drape layer 202 by extending drape layer 202 over and adhering drape layer 202 to foam dressing layer 200 ii) applying disclosing liquid 210 with a refractive index within a range of the refractive index of drape layer 202, wherein the selectively-transparent drape layer 202 changes from a first opaque state 206 to a second transparent state 208, iii) observing treatment site 204 while drape layer 202 remains in second transparent state 208, and iv) allowing disclosing liquid 210 to evaporate, whereby drape layer 202 enters a third, opaque state 212.

Following the disclosed method, in one use of the method, a patient could limit visibility of the treatment site to moments when they are being examined by a medical practitioner. A medical practitioner or clinician may use this method to monitor healing at periwound 205 or on a wound bed or treatment site 204, and then return drape layer 202 to opaque state 212 after an appointment or office visit is complete. This method is partially designed to alleviate patient stress and anxiety associated with viewing severe wound beds when recovering from a traumatic or acute injury.

The method further may include negative pressure wound input device 214 coupled to system 20. Negative pressure wound input device 214 may couple to hole 216 in drape layer 202, through which air may be withdrawn from treatment site 204.

While various illustrative embodiments of the invention are described above, it will be apparent to one skilled in the art that various changes and modifications may be made herein without departing from the invention. The appended claims are intended to cover all such changes and modifications that fall within the scope of the invention.

We claim:

1. A wound therapy system comprising:
a conformable foam dressing layer; and
a conformable drape layer configured to extend over and adhere the conformable foam dressing layer to a treatment site, the conformable drape layer comprising at least two layers of polymeric polarizing filter;
wherein in a first state, the conformable drape layer is opaque;
wherein in a second state, the conformable drape layer becomes transparent when a disclosing liquid with a refractive index within a range of the refractive index of the conformable drape layer is applied to the conformable drape layer; and
wherein in a third state, the conformable drape layer becomes opaque as the disclosing liquid evaporates.

2. The wound therapy system of claim 1, wherein the conformable drape layer comprises a fabric comprising fine fibered polymers.

3. The wound therapy system of claim 2, wherein the fine fibered polymers comprise elastic materials.

4. The wound therapy system of claim 3, wherein the elastic materials comprise polyvinylidene fluoride (PVF), polyvinylidene difluoride (PVDF), ethylene-vinyl acetate, thermoplastic polyurethane, thermoplastic elastomer, thermoplastic vulcanizate, polyether block amide, polyamides, polyethyleneimines, or polyester.

5. The wound therapy system of claim 2, wherein the fine fibered polymers are plasma or corona surface treated.

6. The wound therapy system of claim 2, wherein the fine fibered polymers comprise diameters from about less than 1 micrometer to about 30 micrometers, and wherein the polymers are manufactured from dry laid, airlaid, or woven manufacturing methods.

7. The wound therapy system of claim 1, wherein a patient facing side of the conformable drape layer further comprises an about 5 micrometer to about 20 micrometer breathable polyurethane coating to enhance water proofing.

8. The wound therapy system of claim 1, wherein the conformable drape layer comprises porous or microporous particles, and the porous or microporous particles comprise minerals or polymers, and wherein the minerals comprise silica, silicates, fluorites, or fluorides, and the polymers comprise fluoropolymers, silicones, or acrylics.

9. The wound therapy system of claim 1, wherein the disclosing liquid comprises a refractive index range between about 1.0 and about 2.0.

10. The wound therapy system of claim 1, wherein the disclosing liquid comprises a refractive index range between about 1.2 and about 1.75.

11. The wound therapy system of claim 1, wherein the disclosing liquid comprises a refractive index range between about 1.33. and 1.55.

12. The wound therapy system of claim 1, wherein the disclosing liquid comprises fluorinated ethylene propylene polymer (FEP).

13. The wound therapy system of claim 1, wherein the disclosing liquid comprises water or ethanol or any combination of water and ethanol, or comprises ethanol and benzyl alcohol.

14. The wound therapy system of claim 1, wherein the conformable drape layer comprises polyvinylidene difluoride (PVDF) bonded to a drape cover and the PVDF is fused to the drape cover through heat lamination.

15. The wound therapy system of claim 1, wherein foam pore sizes are less than or equal to 100 micrometers, wherein the conformable drape layer is also a foam and also comprises foam pore sizes less than or equal to 100 micrometers.

16. The wound therapy system of claim 1, wherein the conformable drape layer further comprises a pH indicator, and wherein the pH indicator comprises phenolphthalein.

17. The wound therapy system of claim 16, wherein an acid disclosing agent is wiped over the conformable drape layer, and wherein the acid disclosing agent comprises carbonated water or ethanol in concentration with carbonated water.

\* \* \* \* \*